United States Patent [19]

Paradis

[11] Patent Number: 5,413,558
[45] Date of Patent: May 9, 1995

[54] SELECTIVE AORTIC PERFUSION SYSTEM FOR USE DURING CPR

[75] Inventor: Norman A. Paradis, Brooklyn, N.Y.

[73] Assignee: New York University, New York, N.Y.

[21] Appl. No.: 130,511

[22] Filed: Oct. 1, 1993

Related U.S. Application Data

[63] Continuation-in-part of Ser. No. 756,693, Sep. 9, 1991, Pat. No. 5,334,142.

[51] Int. Cl.⁶ .............................................. A61M 29/00
[52] U.S. Cl. ..................................... 604/101; 600/18; 604/53
[58] Field of Search .................... 600/18; 606/194; 604/23, 28, 49, 53, 96, 97, 101

[56] References Cited

U.S. PATENT DOCUMENTS

| | | | |
|---|---|---|---|
| 4,077,394 | 3/1978 | McCurdy | 600/18 |
| 4,527,549 | 7/1985 | Gabbay | 604/101 X |
| 4,531,936 | 7/1985 | Gordon | 604/49 |
| 4,697,574 | 10/1987 | Karcher et al. | 604/99 X |
| 5,176,619 | 1/1993 | Segalowitz | 600/18 |
| 5,216,032 | 6/1993 | Manning | 514/718 |

*Primary Examiner*—Corrine Maglione
*Attorney, Agent, or Firm*—Browdy and Neimark

[57] ABSTRACT

An apparatus for improving cardiopulmonary resuscitation involves use of a catheter having both an occlusion balloon and a pumping balloon. The occlusion balloon occludes the aorta such that all pumping action will be restricted to the blood vessels above the balloon occlusion. The pumping balloon is cephalad to the occlusion balloon and is preferably pumped in synchronization with external cardiocirculatory resuscitation. The pumping balloon preferably inflates first at the caudal end and then sequentially to the cephalad end in order to provide unidirectional cephalad pumping. Oxygen-carrying fluid may be infused through the lumen into the aorta cephalad of the pumping balloon during use.

19 Claims, 7 Drawing Sheets

SELECTIVE AORTIC PERFUSION SYSTEM FOR USE DURING CPR

CROSS-REFERENCE TO RELATED APPLICATION

The present application is a continuation-in-part of U.S. application Ser. No. 07/756,693, filed Sep. 9, 1991, Now U.S. Pat. No. 5,334,142 the entire contents of which are hereby incorporated herein by reference.

FIELD OF THE INVENTION

The present invention relates generally to treatment of a patient during cardiopulmonary resuscitation (CPR) and more particularly to a process and apparatus for aortic occlusion along with oxygen carrying fluid infusion and/or aortic balloon counterpulsation for use during CPR.

BACKGROUND OF THE INVENTION

Cardiopulmonary resuscitation has not fulfilled its original expectations, and the prognosis for patients remaining in cardiac arrest more than ten minutes remains poor (Becker AB, *Ann Emerg Med*, 20:355 (1991)). Indeed, cardiopulmonary resuscitation has recently been termed a "spectacular failure" in which only a small minority of patients have been successfully resuscitated (Barsan WG, *JAMA*, 265:3115-3118 (1991)). Standard advanced cardiac life support (ACLS) has only limited efficacy after the first few minutes of cardiac arrest. Studies in animal models have shown that vital organ blood flow, and thus oxygen delivery, during CPR is poor (Ditchey RV, et al, *Circ*, 66:297-302 (1982); Ditchey RV et al, *Cardiovasc Res*, 19:419-425 (1985); and Taylor RB, et al, *Resuscitation*, 16:107-118 (1988)). Indeed, CPR generally provides only a small fraction of normal oxygen supply to the brain and heart, and even less to other organs. Recent human studies have confirmed that perfusion pressures, the driving force for organ blood flow, are inadequate in humans during CPR (Paradis NA, et al, *Circ*, 80:361-368 (1989); Paradis NA, et al, *JAMA*, 263:1106-1113 (1990); and Martin GB, et al, *Ann Emerg Med*, 15:125-130 (1986)). High-dose epinephrine, open chest CPR, and cardiopulmonary bypass increase perfusion pressure (Paradis NA, et al, *JAMA*, 265:1139-1144 (1991); Martin GB, et al, *Ann Emerg Med*, 16:628-636 (1987); and Howard MA, et al, *Ann Emerg Med*, 15:664-665 (1986)). However, these are not effective in all patients, or require significant resources not generally available.

In an effort to find simple but effective methods to improve perfusion during CPR, a number of mechanical intravascular based therapies have been investigated. Among these are arterial and venous volume infusion and aortic occlusion (Gentile NT, et al *Crit Care Med*, (1990) (in press); Abu-Nema T et al, *Circ Shock*, 4:55-62 (1988); Suzuki A et al, *Jpn J Anesthesiol*, 29:677-682 (1980); Spence PA, et al, *J Surg Res*, 49:217-221 (1990)); and Manning JEet al, *Ann Emerg Med*, 19:212 (1990). These techniques, however, have failed to improve outcome. Standard aortic counterpulsation that is without distal aortic occlusion, may improve perfusion, but not enough to significantly improve outcome (Emerman CL, et al, *Am J Emerq Med*, 7:378-383 (1989)). Simple balloon occlusion, with or without volume infusion, does not appear to be effective.

It is known to provide oxygenated fluorocarbon emulsions to-transport oxygen to oxygen deprived brain tissue (see U.S. Pat. No. 4,927,623 to Long, Jr.).

Balloon catheter devices and methods are known for directing blood toward the heart during spontaneous circulation (see, for example, U.S. Pat. Nos. 4,407,271 to Schiff; 4,804,358 to Karcher et al; 4,601,706 to Aillon; and 4,459,977 to Pizon et al).

Such catheter devices with two or more balloons are also known (see, for example, U.S. Pat. Nos. 4,531,936 to Gordon; 4,527,549 and 4,741,328 to Gabbay; 4,697,574 to Karcher et al.; 5,176,619 to Segalowitz; and 4,771,765 and 4,902,273 to Choy et al.). None of these devices were designed or intended for use during cardiac arrest.

SUMMARY OF THE INVENTION

It is a primary object of the present invention to provide a process and apparatus for carrying out aortic occlusion along with oxygen carrying fluid infusion to the heart and brain, and/or aortic balloon counterpulsation, as a therapy for cardiac arrest.

It is a further object of the present invention to increase the period of time for possible successful resuscitation during cardiac arrest.

The above objects are accomplished through the use of a specially constructed balloon catheter which, when inflated, occludes the aorta such that fluids infused through the catheter will be restricted to that part of the aorta above the balloon occlusion. An oxygenating fluid (such as either oxygenated perfluorocarbons or stroma-free polyhemoglobin or recombinant hemoglobin) is used as the infused fluid either in a pre-oxygenated state or after an oxygenator has oxygenated the fluid.

In a preferred embodiment of the present invention, the occluding balloon is moved away from the tip of the catheter to make room for a counterpulsation balloon. The counterpulsation balloon is connected to a drive unit outside of the patient by an additional lumen in the catheter. The drive unit is preferably a portable unit which can be carried in ambulances or to various locations in the hospital. A sensor means is added to the tip of the catheter and connected to the external drive unit by a small wire embedded in the catheter wall. The drive unit inflates the counterpulsation balloon when it senses the relaxation phase of CPR, thereby increasing the aortic relaxation pressure which is the primary determinant of outcome during CPR. Because the distal aorta is continuously occluded, all of the increased perfusion is directed cephalad primarily to the heart and brain. In a further preferred embodiment, the balloon is inflated first at its base (caudal end) and that inflation moves cephalad toward the tip. This accelerates oxygen-carrying fluid, either blood or infusate, toward the heart and brain. The occlusion balloon is preferably as close as possible to the caudal end of the counterpulsation balloon.

The combination of the occlusion balloon and the counterpulsation balloon may accomplish the objects of the present invention even without the concomitant infusion of oxygenating fluids through the catheter. Thus, the embodiment of the present invention in which the occlusion balloon is combined with a counterpulsation balloon may be used with or without concomitant oxygen-carrying fluid infusion.

Aortic occlusion with oxygen-carrying fluid infusion will significantly improve oxygen supply for short periods of time to the heart and brain. The infusion of oxygen-carrying fluid will be retrograde up the descending aorta toward the head resulting in preferential infusion of the coronary and carotid arteries. Attempts at defibrillation after this period of improved perfusion of the cardiac muscle will result in significantly higher rates of return of spontaneous circulation when compared to standard CPR.

Furthermore, aortic occlusion, in combination with standard cardiopulmonary resuscitation (CPR) techniques which trigger counterpulsation by a counterpulsation balloon will also result in preferential circulation of blood into coronary and carotid arteries so that attempts at defibrillation will result in significantly higher rates of return of spontaneous circulation when compared to standard CPR. The combination of aortic occlusion and relaxation phase counterpulsation will result in even better coronary perfusion pressures and myocardial oxygen supply, perhaps even greater than during normal circulation. After return of spontaneous circulation, counterpulsation, and/or occlusion, can be continued in its standard mode to improve myocardial perfusion during the initial unstable period that often follows cardiac arrest.

Placement of a balloon catheter in the descending aorta through the femoral artery is not difficult (Bregman D, et al. *Am J Cardiol*, 46:261-264 (1980)) and it may be possible to accomplish this even in a prehospital setting.

The catheter which is used for the present invention is specially designed so as to have a large infusion port. Known balloon catheters have an infusion lumen which is relatively small, designed for the delivery of drugs or small amounts of fluid or for measurement of blood pressure. The catheter of the present invention must be designed to permit the flow of large amounts of perfusion fluid.

The catheter which is used in accordance with the present invention for simultaneous aortic occlusion and CPR relaxation phase counterpulsation is also specially designed. The occluding balloon is moved away from the tip of the catheter to make room for the counterpulsation balloon. One or more additional lumens serve the counterpulsation balloon to cause inflation. In a preferred embodiment, these lumens are also used for active balloon deflation. Active deflation will augment flow from the left ventricle during compression phase of CPR and improve cardiac output. The occlusion balloon is preferably as close as possible to the base of the counterpulsation balloon. If the counterpulsation balloon is segmented in order to cause a wave-like motion during inflation, which would cause a directional pumping activity toward the carotid and cardiac arteries, the occlusion balloon may, indeed, be the first segment of the counterpulsation balloon, which segment is not deflated during the counterpulsation pumping cycle. Unlike counterpulsation devices intended for use during spontaneous circulation, the portion of the present device serving as the occlusion balloon must be capable of inflating to the extent of occluding the aorta so as to maximize perfusion volume and pressure.

A sensor, such as a micromanometer, is preferably added to the tip of the catheter in order to sense the chest compression phase of CPR. Such a micromanometer will trigger off the changes in intravascular pressure generated by chest compression. Alternatively, the central infusion lumen may be used, when infusion is not occurring, to transmit central aortic pressure to an external pressure transducer, which may control the drive unit. A drive unit controlled by a signal from the micromanometer or external transducer is designed to inflate the counterpulsation balloon when it senses the drop in pressure at the beginning relaxation phase of CPR. The counterpulsation balloon is preferably designed in such a way that the balloon is inflated first at its base and that inflation moves cephalad toward the tip. Because the drive unit need not be triggered by variable and complicated electrocardiograph signals, but only a simple signal from a micromanometer, the drive unit may be greatly simplified from normal cardiopulmonary balloon assist drive units. Only one pattern of inflation, cephalad relaxation phase inflation and compression phase deflation, may be required. This will simplify downsizing of such a drive unit to permit portability. This drive unit may be incorporated in existing devices intended to inflate external vests that provide CPR. A combination of the two drive units would coordinate optimization of external CPR and internal intravascular circulation.

As the success of defibrillation in return to spontaneous circulation will be greatly improved after the selective aortic perfusion or circulation of the present invention, it is expected that the process and apparatus of the present invention will supplant CPR alone and will be used in all emergency departments and other critical care areas, and potentially in all advanced life support ambulances.

The present invention further comprehends a kit for use in performing the process of the present invention, which kit will include a catheter, a supply of stroma-free polyhemoglobin (or other oxygen-carrying perfusion fluid) and, optionally, an oxygenator to cause oxygenation of the fluid prior to perfusion through the catheter. The kit will preferably also include all of the other paraphernalia for carrying out the process of the present invention.

BRIEF DESCRIPTION OF THE DRAWINGS

The above and other objects will be shown in more detail in the following detailed description of the preferred embodiments when read in conjunction with the attached drawings, in which.

DETAILED DESCRIPTION OF THE PREFERRED EMBODIMENTS

Figure 1:
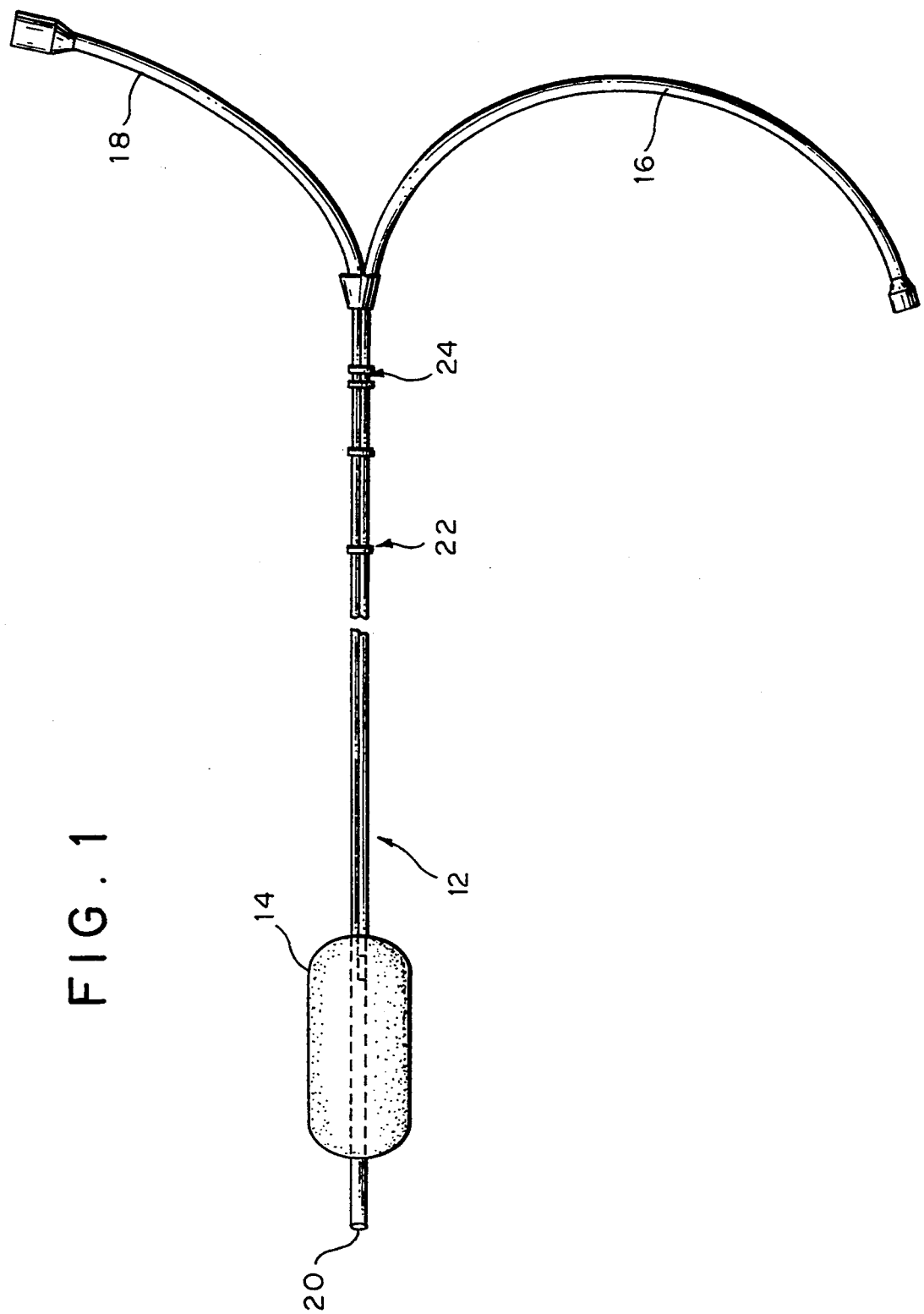
FIG. 1 is a schematic representative cross-section of a balloon catheter which can be used in accordance with the present invention.
Figure 5:
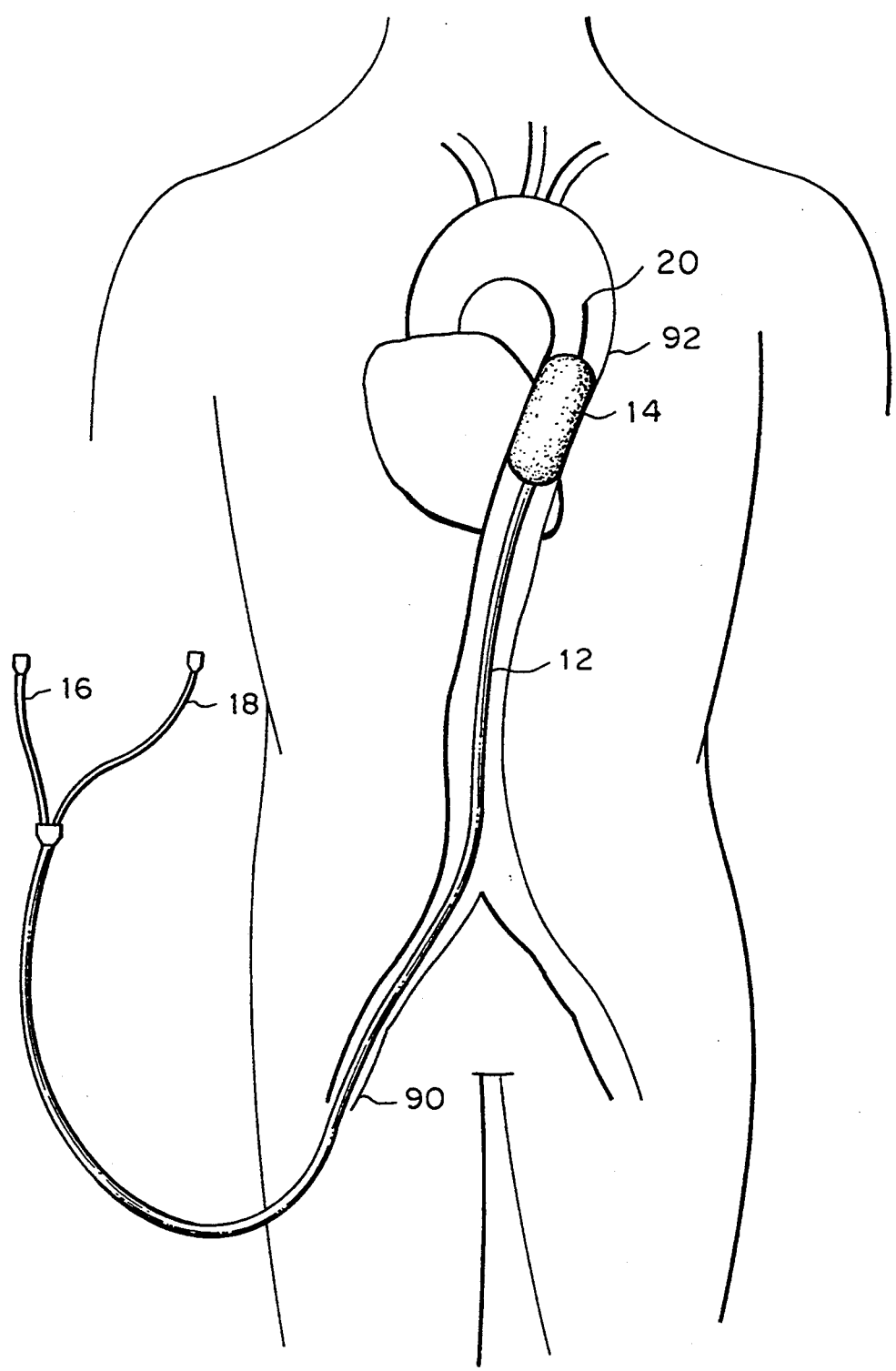
FIG. 5 is a diagrammatic representation showing the catheter in appropriate position during use.

In a first embodiment of the present invention, the selective aortic perfusion system of the present invention has three major components. The first is a specially constructed balloon catheter 12 as shown in FIG. 1. This catheter is sized and dimensioned to permit insertion through the femoral artery and feeding up into the aorta until the balloon 14 is located in the descending aorta. Generally, the medical or paramedical personnel using this invention in an emergency setting will know when the balloon is in appropriate position when the tip of the catheter impacts the top of the aortic arch and cannot easily be maneuvered further through the aorta. Preferably, however, the catheter 12 will include markings 22, 24 which signal the distance from the marking to the tip 20 of the catheter 12 for example, a double mark 24 may mean that the distal tip is 70 cm away with each single mark 22 being in 2 cm increments. The person inserting the catheter 12 will know the position of the balloon 14 in tile aorta from a consideration of the markings at the proximal end of the catheter. When the balloon 14 is in position and is inflated, it will occlude the aorta above the level of the diaphragm (see FIG. 5). Thus, infused fluids will be restricted only to the volume of the aorta and associated arteries above the balloon occlusion.

The catheter 12 is constructed to have two lumens 16, 18. The smaller lumen 16 is used for inflating the balloon. This lumen 16 can be attached to, for example, a 30 cc syringe (not shown) filled with saline. In the rare event of a balloon failure, only saline fluid would be released into the aorta. The larger lumen 18 opens distal to the balloon 18 at a point 20 and is attached to the system for infusion of oxygen containing fluid. The lumens 16, 18 may be side by side or coaxial.

The larger lumen 18 distinguishes the catheter of the present invention from all prior art balloon catheters. The cross-section of this lumen must be large enough to permit sufficient infusion of oxygenating fluid to oxygenate the myocardium and the cerebrum. It has been calculated that to completely replace all of the oxygen deficit which occurs after eight minutes of cardiac arrest, including the ongoing deficit thereafter, a total of four liters of fully oxygenated stroma-free polyhemoglobin would have to be infused over the course of two minutes. It should not be necessary, however, to infuse 100% of the oxygen deficit. Thus, it is fully expected that a replacement of 50% of the oxygen deficit, i.e., two liters of fluid over a course of two minutes, will provide results which are substantially better than standard CPR and yet avoid a possible volume overload when spontaneous circulation returns. Indeed, CPR is occasionally successful despite providing significantly less oxygen supply. Thus, 0.25-1.5 liters will most probably be sufficient in practice, up to a maximum of 3 liters (when fully oxygenated SFPH is used as the fluid) over the course of about one to three minutes.

The appropriate size lumen to permit this much infusion over the specified time period can be designed using standard engineering formulas, such as Poiseuille's Law, and/or empirical testing. The optimum diameter is on the order of about 2-3 mm so as to permit infusion without using excessive feed pressure while maintaining the catheter as a whole sufficiently small to permit insertion through the femoral artery. It is believed that the largest existing balloon catheters have an inner lumen of less than about 1 mm. For some applications, such as pediatric applications, the diameter may be as small as 1.5 mm and could be as large as 4 mm. Catheters of this large size can be easily placed using existing guide wire/introducer sheath techniques.

The most important function of the oxygenating fluid is to perfuse the myocardium, thereby permitting a vastly improved chance of return to spontaneous circulation after defibrillation. It is a secondary function to oxygenate the brain in order to prevent damage to the brain during the period of cardiac arrest. However, a prompt return to spontaneous circulation after perfusion of the myocardium and defibrillation will serve the purpose of oxygenating the cerebrum much better than the perfusion of oxygenating fluid in accordance with the present invention. In order to increase the amount of perfusion of the myocardium and cerebrum, it may be desirable to actually prevent flow of the perfusion fluid to the upper extremities by applying pressure to the appropriate arteries during infusion of the fluid. Furthermore, while it is permissible to continue CPR throughout the procedure of the present invention, it is permissible to suspend CPR once the catheter has been inserted, as the perfusion being caused by the infusion of oxygenating fluids will be much greater than that caused by the CPR. It may be desirable to leave the balloon fully or partially or partially inflated after return of spontaneous circulation to continue preferential perfusion of the brain and heart.

The second component of the system of the present invention is oxygenating fluid. Currently, there are two types of artificial fluids which are used to carry oxygen for use in humans. The first is oxygenated perfluorocarbons and the second is stromafree polyhemoglobin (SFPH) or recombinant hemoglobin. SFPH has recently been approved for preliminary human testing and is available from the Biopure Company.

Figure 2:
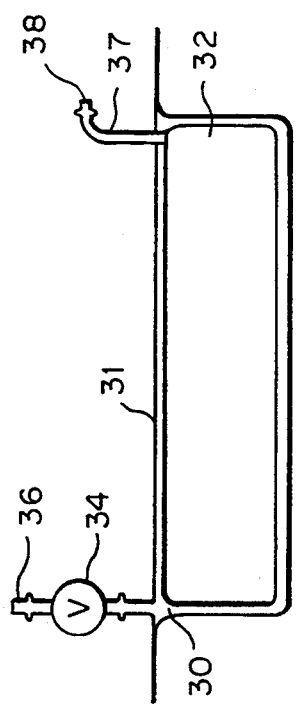
FIG. 2 is a schematic representative cross-section of a pressurizable container for use in dispensing oxygenatable fluid.

The oxygenating fluid solution is preferably packaged in a special container capable of being pressurized, as shown in FIG. 2 so that it can be infused at pressures necessary to overcome those during the compression phase of CPR and necessary to provide a sufficient flow rate of oxygenating fluid. The oxygenating fluid is stored in a pressure bag 32, preferably in a quantity of 500 cc or more. The bag is placed in a container 30 having a lid 31 sealed thereto. An inlet valve 34 in the lid 31 of the container includes a regulator mechanism (the details of which are well known and not shown) which permits entry of pressurized fluid at a specified maximum pressure regardless of the pressure of the fluid at the inlet of the valve 34. The valve 34 includes an inlet nozzle 36 which is connectable to the source of standardized pressurized oxygen available in all emergency and critical care settings. While pressurized oxygen is the preferred source of pressurized fluid to drive the feeding of the oxygenating fluid, it is to be understood that any other source of pressurized gas or liquid could be used for this purpose.

An outlet tube 37 connected to the interior of the bag 32 extends from the container 30 and includes a connector 38 for connection to the oxygenating fluid feeding lumen 18 of the catheter 12.

While the special container described above is the preferred means of dispensing the oxygenating fluid solution, it should be understood that this particular means is not critical and that any manner of supplying the oxygenating fluid under pressure sufficient to provide the desired amount of infusion over the predetermined period of time can be used in the method of the present invention.

The oxygenating solution may also include the simultaneous infusion of other drugs or agents to improve myocardial and cerebral outcome. Any agent demonstrated to be effective when given intravenously may be more effective when administered to the heart and brain selectively by means of the present invention. Tissue salvaging agents in particular may be included in the oxygenated infusion fluid. Examples of agents which may be included in the oxygenated infusion fluid of the present invention are: epinephrine or other adrenergic agonists and pressors; antioxidants and free-radical scavengers such as the 21-amino steroids (lazaroids); anti-inflammatory agents including steroids and non-steroidal anti-inflammatory drugs such as a ibuprofen; calcium channel blockers such as lidoflazine, nimodipine, nicardipine, flunarizine, etc.; excitatory neurotransmitter blockers (NMDA receptor agonists) such as MK801, etc.; anticoagulants such as heparin; iron and heavy metal chelators such as deferoxamine; osmotic agents such as mannitol; anti-acidosis agents such as bicarbonate or dichloroacetate; insulin; antibodies such as anti-neutrophile antibody; and allopurinol. This list is intended to be exemplary only and not limiting.

Figure 3:
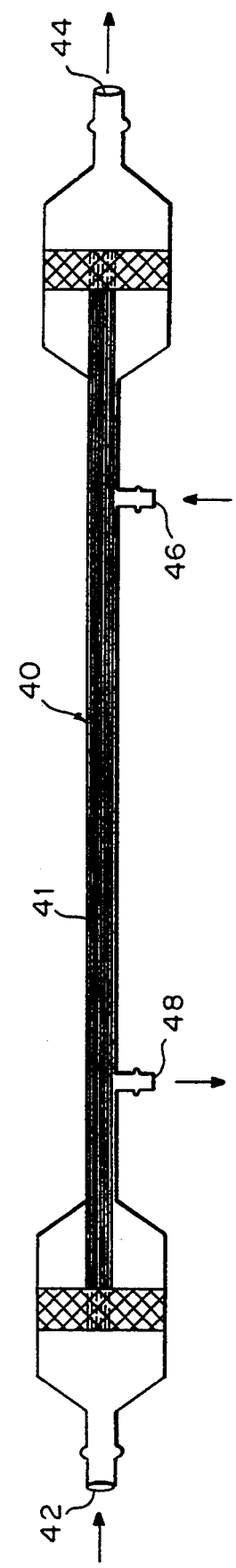
FIG. 3 is a schematic representative cross-section of an oxygenating system for use with the present invention.

The third component of the system of the present invention is an apparatus to oxygenate the oxygenating fluid before infusion. This component is optional as the oxygenating fluid may be supplied already oxygenated and ready to use. However, as the oxygenating fluid may lose its oxygen over storage time it is preferred that the fluid be freshly oxygenated immediately prior to perfusion. Simple infusion of the solution into the arterial side of the circulation without pre-oxygenation would not improve the delivery of oxygen to the myocardium and brain. As shown in FIG. 3, a hollow fiber membrane oxygenator 40 having hollow fibers 41 can be placed in the system between the pressurized container 30 of oxygenating fluid, at in-port 42 and the lumen 18 of the balloon catheter 12 at out-port 44. These systems allow the blood to flow around numerous hollow fibers 41 which have been specially constructed to allow diffusion of gas phase components without leakage of oxygenating fluid or blood. Oxygen is forced in at in-port 46 and exits at out-port 48. The mechanism of oxygenation is preferably countercurrent, which should result in oxygenation of the stroma-free polyhemoglobin, or other oxygenating fluid, to its maximum saturation. This device will also be constructed so that standard oxygen tanks or other emergency room oxygen supply can be used to supply it. The same oxygen can be used to inflate the pressure bag and drive the infusion as is used to oxygenate the fluid.

Figure 4:
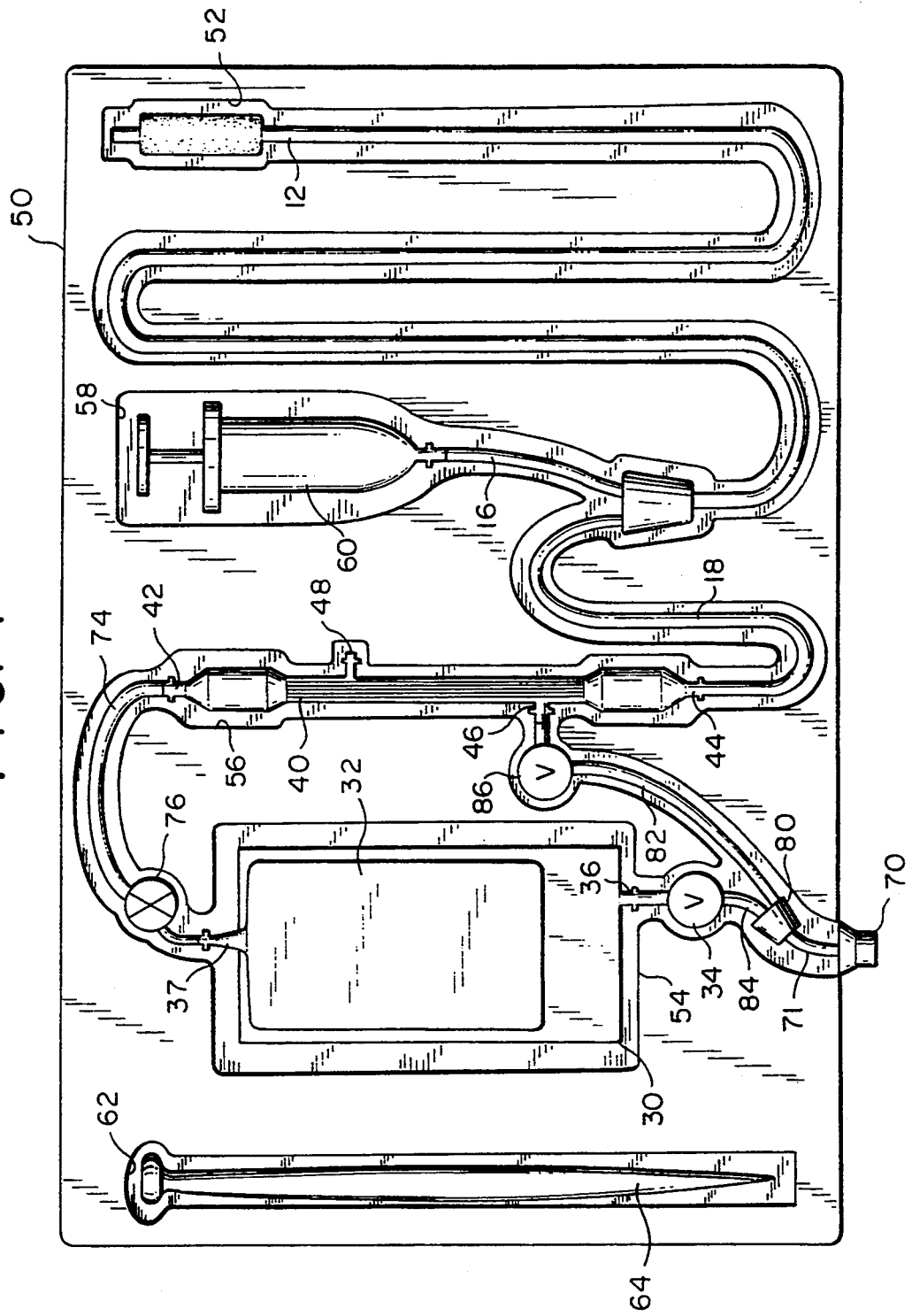
FIG. 4 is a diagrammatic representation of a kit in accordance with the present invention.

The components of the present invention are preferably packaged in kit form for use by medical and paramedical personnel. The components of the kit are preferably packaged in a sealed container which is compact and portable and suitable for use by emergency room or ambulance medical or paramedical personnel. As shown in FIG. 4, the components may be packaged in a container 50, preferably a rigid plastic material molded to provide compartments for the various components of the kit. Compartment 52 holds the catheter 12, compartment 54 holds the container 30 with the sack 32 of oxygenating fluid (or compartment 54 may comprise the container 30 and hold only the sack 32), and compartment 56 holds the oxygenator 40. Compartments for other paraphernalia necessary to implement the process of the present invention may also be present. For example, compartment 58 may be present for holding a syringe 60 to be used for inflation of the balloon and compartment 62 may be present to hold a catheter insertion sheath 64. Other components such as oxygenation tubing, guide wires, instructions for use, etc., may also be present.

The preferred kit form for use in the present invention is one which is the simplest and easiest to use in an emergency situation, which is often somewhat chaotic. Thus, the connections between the oxygenator and the source of oxygenating fluid may be built-in so that the source of oxygenating fluid and the oxygenator need never be removed from the kit. Similarly, the connection between the oxygen output of the oxygenator and the pressure chamber of the oxygenating fluid compartment may be built into the kit, as may the connection between the balloon syringe and the catheter lumen leading to the balloon and the connection between the oxygenator fluid output and the catheter lumen for feeding the oxygenating fluid.

For example, as shown in FIG. 4, the oxygenator 40 may be sealed within the kit 50 with only an appropriate oxygen input nozzle 70 extending from the container. Nozzle 70, which extends from container 50 may be a standard connector for connection to a source of pressurized oxygen such as a standard oxygen tank or other emergency room oxygen supply. The nozzle 70 is connected within the container 50, by means of tube 71, to a Y-junction 80 which divides the oxygen input into line 82, which leads to the oxygen in-port 48 of the oxygenator, and line 84, which leads to the pressurizable container 30. The oxygen out-port 48 of the oxygenator may be vented to the atmosphere. All of these lines may be sealed within the container 50. The regulator valve 34 is also present within the container 50 so as to regulate the maximum pressure of fluid entering the container 30 for pressurizing the sack of oxygenating fluid 32. A rubber or plastic pressure bladder, not shown, may be placed between the sack 32 and the pressure chamber 30 to diminish risk of damage to sack 32. A second regulator valve 86 may also be built-in at the oxygen in-port 46 of the oxygenator 40 in order to regulate the pressure of oxygen entering the oxygenator 40.

The output port 37 from the sack 32 of oxygenating fluid may be directly connected to the oxygenating fluid inlet port 42 of the oxygenator 40 by means of a tube 74 sealed within the container 50. A valve 76, accessible from the outside of the container 50, may be used to open or close access of the oxygenating fluid from the sack 32 to the oxygenator input 42. The output from the oxygenator 40 through the out-port 44 may be directly connected to the fluid input cannula 18 of the catheter 12. Thus, no physical connections need be made by the emergency personnel except for attachment of an oxygen source to nozzle 70.

In use, the catheter 12 is removed from the compartment 52 of the kit. Lumen 18, which is much longer than is schematically shown in FIG. 4, is already connected to the output 44 of the oxygenator. Lumen 16 is also already connected to the syringe 60. Syringe 60 is preferably one which contains exactly the right amount of fluid to cause inflation of the balloon and is constructed so as to permit one-time use only. The use of such a pre-packaged syringe will eliminate the possibility of over-inflation and rupture of the balloon. A source of pressurized oxygen is connected to the nozzle 70 of the container 50.

The femoral artery 90 (see FIG. 5) will be punctured by a needle, through which a guide wire is advanced into the descending aorta 92. The guide wire may be any standard flexible guide wire or it could be a specially designed guide wire of increased stiffness to facilitate placement directly up the aorta. An introducer sheath 64 is removed from the compartment 62 of the container 50 and then advanced over the wire into the femoral artery. The central trochar and the guide wire are removed from the introduced sheath and the distal end 20 of the catheter 12 is introduced through the sheath into the femoral artery and fed until the balloon reaches the appropriate position in the aorta as determined by the markings 22 and 24 on the catheter or by other known means. Alternatively, the guide wire can be left in place to facilitate placement of the catheter 12, the guide wire being removed after placement of the catheter 12. The balloon 14 is then inflated by means of the syringe 60 and the valve 76 is opened in order to permit the feeding of the oxygenating fluid through the oxygenator 40 and into the lumen 18 and opening 20 into the aorta at the predetermined flow rate. At the same time, oxygen will flow through the oxygenator, countercurrent to the flow of oxygenating fluid, and into the pressure chamber 30 to drive the flow of oxygenating fluid at the predetermined rate, determined by the regulator valve 34. The oxygen output from the oxygenator may include a bleed valve to ensure flow of oxygen through the oxygenator even when not necessary for pressurization of the chamber 30.

Figure 6:
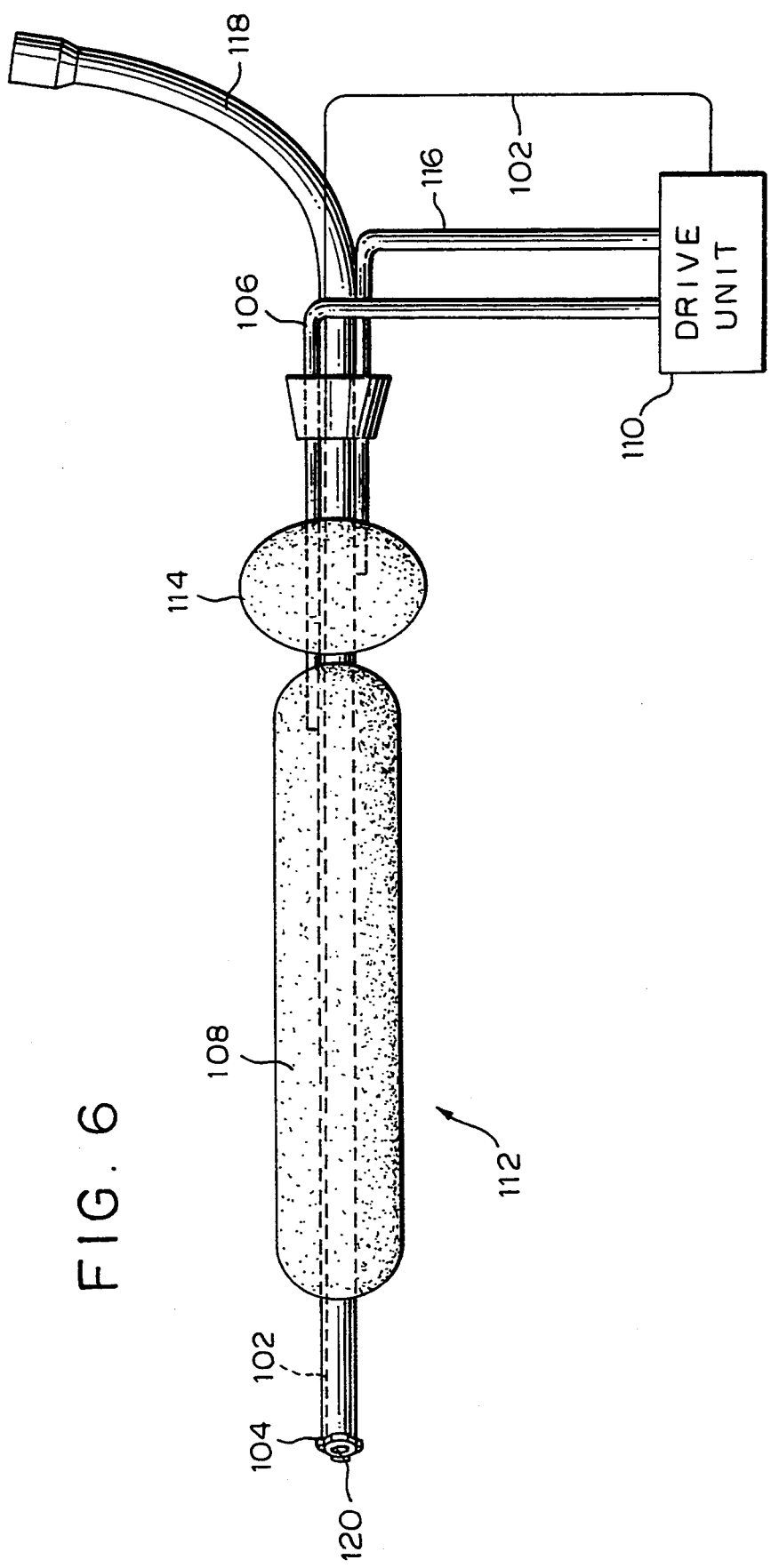
FIG. 6 is a schematic representative cross-section of a balloon catheter which can be used in accordance with a second embodiment of the present invention and which includes aortic balloon counterpulsation.
Figure 7:
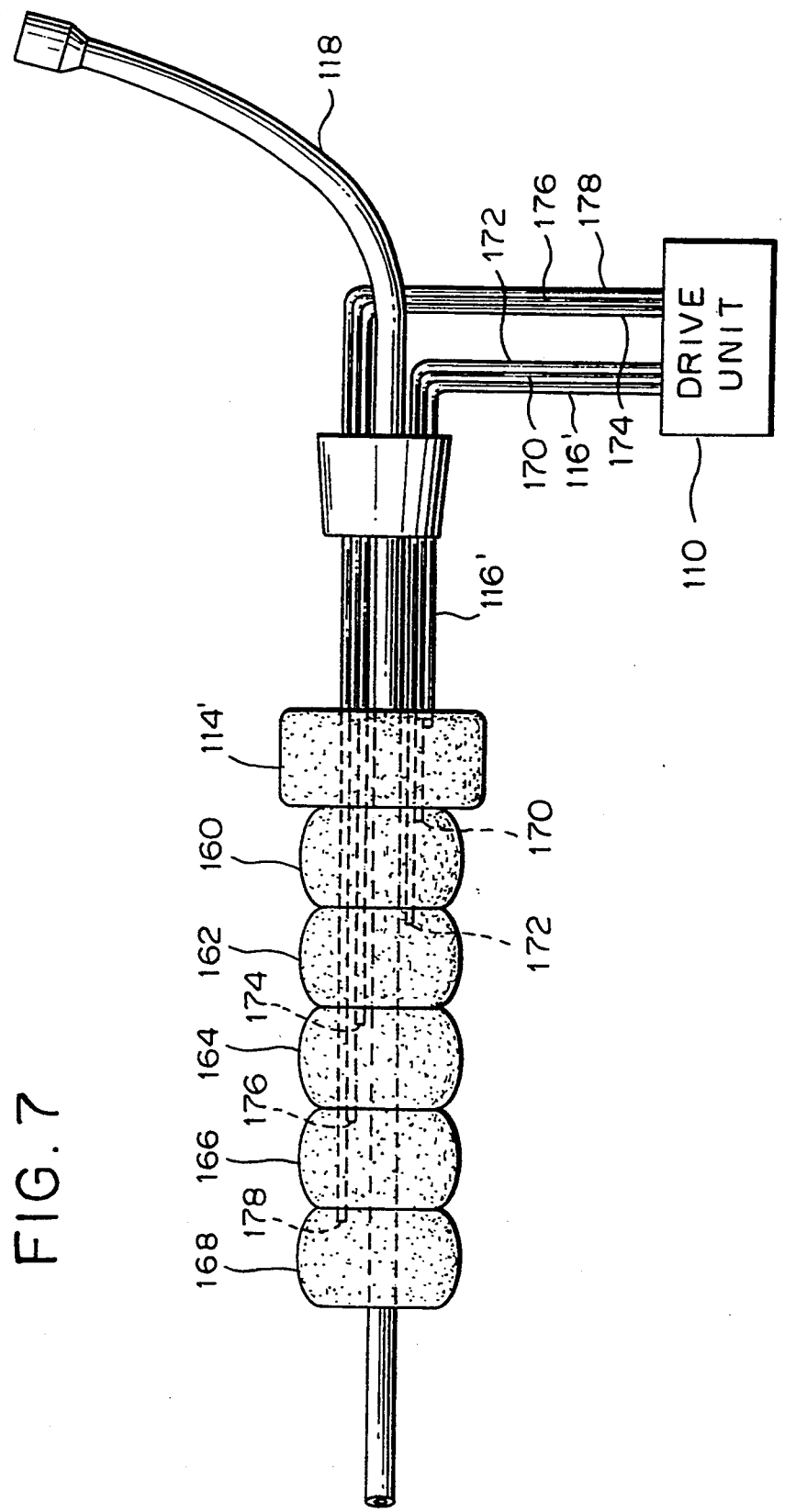
FIG. 7 is a schematic representative cross-section of another embodiment of an aortic balloon counterpulsation catheter.
Figure 8:
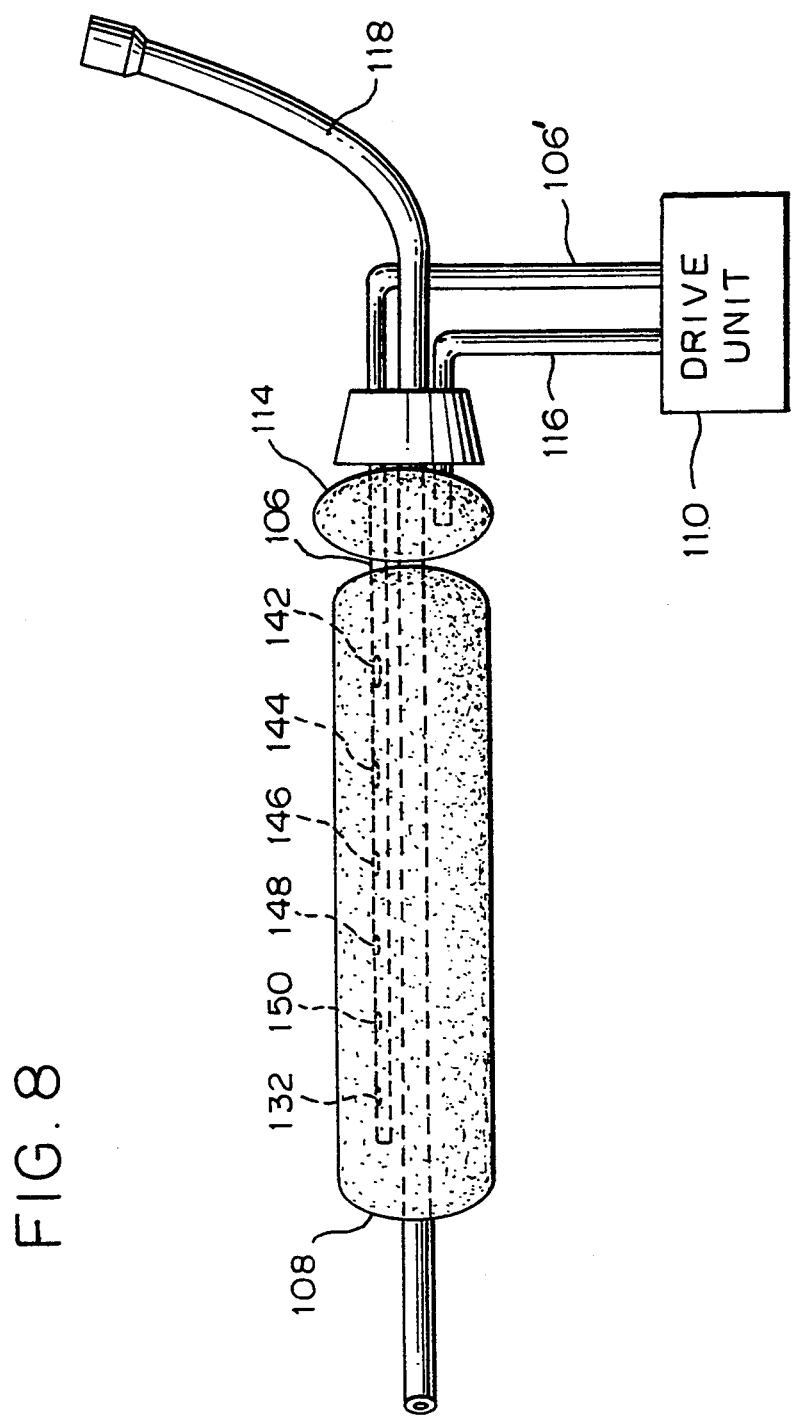
FIG. 8 is a schematic representative cross-section of yet a further embodiment of an aortic balloon counterpulsation catheter.

Another embodiment of the present invention is illustrated in FIGS. 6-8. In the embodiment illustrated in FIG. 6, the catheter 112 is substantially similar to the catheter 12 of FIG. 1. With respect to the occlusion balloon 114 which corresponds to the balloon 14 of FIG. 1, smaller lumen 116, which is used for inflating the occlusion balloon 114 and corresponds to the smaller lumen 16 of the catheter 12 of FIG. 1 and the larger lumen 118, which corresponds to the larger lumen 18 of FIG. 1. However, in the embodiment of FIG. 6, the occlusion balloon 114 is moved away from the tip 120 of the catheter and a counterpulsation balloon 108 is disposed on the catheter 112 between occlusion balloon 114 and the distal tip 120. Occlusion balloon 114 preferably has a diameter sufficient to fill the aortic lumen when inflated. A third lumen 106 is also made part of the catheter 112 to inflate the counterpulsation balloon 108. The three lumens 116, 118 and 106 may be side-by-side or coaxial.

At the distal tip of the catheter 112 is a micromanometer 104 capable of sensing the chest compression phase of CPR. A wire 102 is connected to the micromanometer 104 and is embedded in the wall of the catheter 118.

A drive unit, schematically shown at 110, drives the operation of the counterpulsation balloon 108. Thus, the lumen 106 which feeds inflating fluid (either liquid or gas) to the counterpulsation balloon 108 is connected to this drive unit as is the wire 102 which is connected to the micromanometer. The drive unit is designed such that, when the micromanometer senses the relaxation phase of CPR, the drive unit causes inflating fluid to pass through the lumen 106, thereby inflating the counterpulsation balloon 108. In a preferred embodiment, the drive unit also causes active deflation of the counterpulsation balloon 108 by actively removing fluid therefrom when the micromanometer senses the beginning of the compression phase of CPR. In the embodiment shown in FIG. 6, the occlusion balloon 14 is also connected to the drive unit 110. The drive unit 110 maintains the occlusion balloon 14 continuously in an inflated position. The occlusion balloon may also be filled separately by syringe.

When the counterpulsation balloon is being used in combination with CPR, it is not necessary to infuse oxygenating fluid through the catheter 118 in order to improve oxygenation of the heart and brain. Thus, it is not necessary that the catheter 118 be as large as is described above for the embodiment of FIG. 1. Indeed, this lumen may be of standard size and used only for injection of drugs. Alternatively, oxygenating fluid can be perfused simultaneously with the counterpulsation CPR in order to even more greatly increase the volume and oxygenation content of the fluid reaching the heart and the brain during this operation. In another embodiment, the micromanometer 104 may be omitted and the balloon 108 used only as a pump mechanism to assist in the infusion of the oxygenating fluid through the lumen 118 without external CPR. For this embodiment, it is important only that the pulsation balloon 108 be driven in such a way as to allow alternating caridac output and aortic pulsation. In this embodiment, it is being used solely as a pump.

In another preferred embodiment of the present invention, the counterpulsation balloon 108 is designed so as to preferentially inflate, beginning at the caudal end, i.e., the end closest to the occlusion balloon 114, and then continuously inflate toward the distal end. This will cause the fluid to be pumped unidirectionally in a cephalad direction, primarily to the heart and brain. This will also prevent excessive pressure build-up in the aorta between the counterpulsation balloon 108 and the occlusion balloon 114. This unidirectional inflation of the counterpulsation balloon 108 may be accomplished in any of various manners. In the embodiment shown in FIG. 6, it is accomplished by placing the outlet of the lumen containing the inflation fluid at the caudal end of the balloon so that inflation will commence at that end and proceed cephalad toward the distal end of the catheter.

Other means may also be used to achieve this unidirectional pumping function. For example, as shown in FIG. 7, the counterpulsation balloon may be segmented into segments 160, 162, 164, 166 and 168. Each segment is served by a respective one of a plurality of lumens 170, 172, 174, 176, 178. The lumens are supplied with fluid in such a programmed way that the caudal segments inflate before the next cephalad segment inflates. In this embodiment, the occlusion balloon 114' may be the first segment of such a segmented balloon, or the first balloon of a series of balloons, which first segment remains continuously inflated. The remaining segments are inflated in a wave-like motion to cause unidirectional wave-like inflation in a cephalad direction. Thus, segment 160 is first inflated by means of its lumen 170, followed by inflation of segment 162 by means of its lumen 172, followed in turn by inflation of segment 164, 166 and 168 by means of their respective lumens 174, 176 and 178. Proper order and speed inflation is all controlled by drive unit 110 by means which will be readily apparent to those of ordinary skill in this art. The active deflation may be simultaneous or sequential for segments other than the segment which serves as the occlusion balloon 114.

Another way of obtaining unidirectional inflation is shown in FIG. 8. In this embodiment, the lumen 106' extends throughout the length of the counterpulsation balloon 108. The lumen 106' has a plurality of openings 142, 144, 146, 148, 150, 152. In order to permit unidirectional inflation, the multiple openings are designed with variable resistance, such that the openings at the caudal end have the least resistance and the openings at the cephalad end have the most resistance. As shown in FIG. 8, the opening 142 at the proximal or caudal end of the lumen 106' within the balloon 108 is larger than the next distal opening 144, which, in turn, is larger than the next distal opening 146, etc. Thus, fluid will fill the caudal end of the balloon 108 first, causing unidirectional inflation.

A further way of achieving unidirectional inflation is by causing progressively greater reinforcement to the balloon from the caudal to the cephalad end thereof, so that the non-reinforced caudal end will present the least resistance to inflation and will inflate first with the more reinforced cephalad end, having a greater resistance to inflation, inflating last.

In another preferred embodiment of the present invention, the fluid is removed from the counterpulsation balloon by active deflation. That is, the fluid is actively withdrawn from the counterpulsation balloon during deflation from outside of the catheter, such as by means of the drive unit 110, by pulling a suction through the lumen 106 to cause the fluid to be removed from the balloon and enhance or speed up the deflation. In this way, deflation need not depend solely on the elasticity of the balloon material and, indeed, the balloon material need not even be elastic. Even if the balloon material is elastic, active deflation will further assist in the rapid and total deflation of the counterpulsation balloon 108, thereby improving circulation.

In the embodiment shown in FIG. 6, active deflation may cause occlusion of the outlet opening of lumen 106 by the balloon before all of the fluid is removed therefrom. Accordingly, an embodiment such as that of FIG. 7 or FIG. 8 is preferred when active deflation is being used.

In the embodiment of FIG. 8, active deflation may cause the caudal end of the balloon 108 to deflate first, but this should not be a problem, as directionality or non-directionality is not as important during deflation as it is during inflation. In the embodiment of FIG. 7, active deflation can be programmed in any order so that all of the segments may be deflated simultaneously or the cephalad segment may be deflated first in order to cause a wavelike deflation opposite to the wave-like inflation, if so desired.

Another advantage of active deflation is that the movement of blood from the left ventricle during the compression phase of CPR may be augmented by the antegrade flow caused by the active deflation of the balloon. In other words, deflation of the balloon will actually help to draw liquid from the left ventricle, further augmenting the effectiveness of the CPR.

The fluid serving the counterpulsation balloon or balloons is preferably a gas, such as $CO_2$ or helium. For the reasons discussed above, a liquid such as saline would be preferred for safety purposes, but because of the large volume of fluid which must pass through the openings of the lumens in short periods of time during counterpulsation, there is usually too much resistance when using a liquid. Carbon dioxide, helium, or any other gas that is rapidly absorbed into blood, are the preferred gases because a leak of such gases into the aorta would not cause catastrophic effects, as would occur if air were leaked in.

While the embodiments of FIGS. 6–8 show the lumen 116 which serves the occlusion balloon 114 to be driven by the drive unit 110, it should be understood that this lumen may be separately controlled, as there is no need for programmed inflation and deflation of the occlusion balloon.

It should further be understood that any type of sensor which can sense the pressure being applied to the chest during CPR may be used, as the sensor 104 in place of a micromanometer. Those of ordinary skill in the art will be aware of other types of sensor devices which can serve the same purpose.

In operation, the catheter 112 will be inserted into the femoral artery in the same manner as discussed above with respect to FIG. 5. In order to prevent damage to the aorta, the distal tip of the catheter 112 should be placed just short of the aortic arch. Partially inflating the counterpulsation balloon(s) during insertion may facilitate placement in the aortic arch, should this be desired, although there may be some risk of entering a second order artery, such as the carotid. The occlusion balloon 114 may be disposed anywhere in the descending aorta which is cephalad to the celiac arteries. The counterpulsation balloon 108 disposed between the occlusion balloon 114 and the distal tip of the catheter is preferably longitudinally extended in order to create as much power as possible in the unidirectional pumping action.

Once in place, the occlusion balloon 114 is inflated, either by means of the drive unit 110 or by means of a syringe as described with respect to the embodiment of FIG. 1. When the micromanometer 104 senses the relaxation phase of CPR, the drive unit 110 causes inflating fluid to pass through the lumen 106, thereby inflating the counterpulsation balloon 108. When the micromanometer senses the commencement of the compression phase, the drive unit actively withdraws the fluid from the counterpulsation balloon 108, thus actively removing the fluid therefrom, causing rapid deflation, thereby assisting in the removal of blood from the left ventricle during the compression phase of CPR. Throughout the CPR, oxygenating fluid may be fed through the larger lumen 118. In a preferred embodiment, the infusion of oxygenating fluid will be timed to correspond to the relaxation phase of CPR, while the counterpulsation balloon is unidirectionally inflating, thus forcing a larger volume of blood and oxygenating fluid into the cardiac and carotid arteries. This phased infusion of the oxygen carrying material may be accomplished by the external drive unit or by coordinating with it.

Once spontaneous beating of the heart is resumed, the occlusion balloon 114 is deflated in order to permit blood to be delivered throughout the body. The counterpulsation balloon may continue to operate in the normal mode of a circulatory assist pump, particularly when the embodiment shown in FIG. 7 is used, which has greater control over the manner of inflation and deflation of the counterpulsation balloon in the normal mode of cardiocirculatory assist of a spontaneously beating heart, the unidirectional motion may be abandoned and uniform inflation and deflation adopted so that blood will be forced in both directions during operation of the counterpulsation balloon. For this embodiment, the drive unit 110 may include electrocardiograph leads in order to drive the counterpulsation balloon in the normal manner of a cardiocirculatory assist pump once spontaneous beating has commenced.

The system of each of the embodiments of the present invention will be efficacious in the treatment of cardiac arrest and its potential application is quite extensive. As stated previously, standard techniques for the treatment of cardiac arrest are useful only in the initial few minutes. It is believed that rapid application of the selective aortic perfusion system, or the aortic occlusion and CPR counterpulsation technique, of the present invention, will extend the period during which successful resuscitation could be obtained. The systems should prove efficacious and it is believed that emergency departments and other critical care areas, and, potentially, life support ambulances, will be able to easily stock this particular pieces of equipment and use the systems of the present invention.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

I claim:

1. A cardiopulmonary resuscitation counterpulsation balloon and occlusion catheter, comprising:
    a catheter having first, second and third lumens and first and second balloons on the external side thereof, said catheter being sized and dimensioned to permit placement through the femoral artery with the first and second balloons positioned in the descending aorta or aortic arch;
    said second balloon being disposed on said catheter at a position which is closer to the aortic valve than is the position of said first balloon when said catheter is in its intended position in the descending aorta or aortic arch, said first balloon being sized and dimensioned to occlude the descending aorta when the catheter is in use and the first balloon is inflated and said second balloon being sized and dimensioned to cause pumping of fluid in the aorta when the catheter is in use and said second balloon in inflated;
    said first lumen passing through the catheter and opening into the aorta at a position closer to the aortic valve than that of said second balloon when in use;
    said second lumen communicating with the interior of said first balloon for use in inflating said first balloon;
    said third lumen communicating with the interior of said second balloon for use in inflating said second balloon; and
    unidirectional means, connected to said catheter, for causing said second balloon to inflate from the end thereof closest to said first balloon to the opposite end thereof, when in use, thereby providing unidirectional pumping in the direction away from said first balloon.

2. A catheter in accordance with claim 1, further including pressure sensing means for sensing the compression and relaxation phases of external cardiopulmonary resuscitation when in use, disposed on the catheter at a position closer to the aortic valve than that of said second balloon.

3. A catheter in accordance with claim 2, wherein said pressure sending means is a micromanometer.

4. A catheter in accordance with claim 2, further including drive means, connected to said pressure sensing means and to said second balloon, for causing inflation and deflation of said second balloon in synchronization with the sensed phases of external cardiopulmonary resuscitation.

5. A catheter in accordance with claim 1, further including drive means connected to said third lumen, for causing programmed inflation and deflation of said second balloon.

6. A catheter in accordance with claim 5, wherein said drive means is further for causing active deflation of said second balloon by applying negative pressure to the fluid when in use.

7. A catheter in accordance with claim 1, wherein said second balloon has a shape which is elongated in the direction of the longitudinal axis of said catheter and said third lumen opens into the end of said second balloon which is closest to said first balloon when in use, thereby comprising said unidirectional means.

8. A catheter in accordance with claim 1, wherein said second balloon is segmented and wherein said unidirectional means includes means to cause the sequential inflation of the segments of said second balloon.

9. A catheter in accordance with claim 8, wherein said first balloon is adjacent to the segment of said segmented second balloon which is closest to said first balloon when in use.

10. A catheter in accordance with claim 8, wherein said catheter has a plurality of additional lumens, wherein said third lumen communicates with the interior of one of the segments of said second balloon and each of said additional lumens communicates with the interior of a corresponding one of the remainder of the segments of said segmented balloon, whereby the inflation and deflation of each segment of said segmented second balloon may be individually controlled.

11. A catheter in accordance with claim 10, wherein said unidirectional means includes drive means connected to each of said third lumen and said additional lumens, for causing programmed inflation and deflation of said second balloon.

12. A catheter in accordance with claim 10, wherein the inner diameter of said first lumen is about 3 mm.

13. A catheter in accordance with claim 1, wherein said third lumen extends substantially throughout the length of said second balloon and has a plurality of openings therein through which inflation fluid flows when in use, wherein each opening has a greater resistance to fluid flow than the next opening closer to said first balloon said openings thereby comprising said unidirectional means.

14. A cardiopulmonary resuscitation counterpulsation balloon and occlusion catheter, comprising:
    a catheter having first, second and third lumens and first and second balloons on the external side thereof, said catheter being sized and dimensioned to permit placement through the femoral artery with the first and second balloons positioned in the descending aorta or aortic arch;
    said second balloon being disposed on said catheter at a position which is closer to the aortic valve than is the position of said first balloon when said catheter is in its intended position in the descending aorta or aortic arch, said first balloon being sized and dimensioned to occlude the descending aorta when the catheter is in use and the first balloon in inflated and said second balloon being sized and dimensioned to cause pumping of fluid in the aorta when the catheter is in use and said second balloon in inflated;

said first lumen passing through the catheter and opening into the aorta at a position closer to the aortic valve than that of said second balloon when in use;

said second lumen communicating with the interior of said first balloon for use in inflating said first balloon;

said third lumen communicating with the interior of said second balloon for use in inflating said second balloon; and wherein said first lumen has an inner diameter of at least about 1.5 mm.

15. A method for improving cardiopulmonary resuscitation during cardiac arrest, comprising the steps of:

placing a balloon catheter having a lumen therethrough, an inflatable occlusion balloon and an inflatable pumping balloon, in the descending aorta or aortic arch of the patient in cardiac arrest, such that said occlusion balloon is positioned in the descending aorta or arch cephalad to the celiac arteries, said pumping balloon is disposed cephalad to said occlusion balloon and a lumen of the catheter opens into the aorta cephalad to said pumping balloon at or below the aortic arch;

inflating said occlusion balloon to occlude the aorta; and causing programmed inflation and deflation of said pumping balloon, whereby flow of fluid pumped by said pumping balloon is restricted to the blood vessels cephalad to said occlusion balloon.

16. A method in accordance with claim 15, further including the step of infusing an oxygenating fluid through said lumen opening into the aorta cethalad to said pumping balloon.

17. A method in accordance with claim 15, further including the step of applying external cardiocirculatory resuscitation to the patient, and wherein said causing step comprises causing inflation and deflation of said pumping balloon in synchronization with said externally applied cardiopulmonary resuscitation.

18. A method in accordance with claim 15, wherein said inflation of said pumping balloon is affected such that the balloon inflates first at the end thereof nearest to said occlusion balloon and progressively to the opposite end thereof, thereby providing unidirectional cephalad pumping.

19. A method in accordance with claim 15, wherein said deflation of said pumping balloon is effected by actively sucking the inflation fluid from the balloon.

* * * * *